United States Patent [19]

Guy et al.

[11] Patent Number: 5,540,930
[45] Date of Patent: Jul. 30, 1996

[54] SUSPENSION OF LOTEPREDNOL ETABONATE FOR EAR, EYE, OR NOSE TREATMENT

[75] Inventors: Yaacov J. Guy, Rehovot; Doron I. Friedman, Carmei Yosef, both of Israel

[73] Assignee: Pharmos Corporation, New York, N.Y.

[21] Appl. No.: 142,743

[22] Filed: Oct. 25, 1993

[51] Int. Cl.$^6$ ............ A61K 9/10; A61K 47/32; A61K 47/36
[52] U.S. Cl. ............ 424/427; 424/437; 424/434; 514/772.2; 514/772.5; 514/778; 514/914; 514/772.3; 514/937
[58] Field of Search ............ 514/772.3, 772.2, 514/772.5, 778, 914; 424/489, 427, 428, 437

[56] References Cited

U.S. PATENT DOCUMENTS

| | | | |
|---|---|---|---|
| 2,861,920 | 11/1958 | Dale et al. | 167/65 |
| 4,383,992 | 5/1983 | Lipari | 424/238 |
| 4,409,205 | 10/1983 | Shively | 514/912 |
| 4,602,026 | 7/1986 | Awata et al. | 514/912 |
| 4,710,495 | 12/1987 | Bodor | 514/174 |
| 5,089,482 | 2/1992 | Hermens et al. | 514/58 |
| 5,149,693 | 9/1992 | Cagle et al. | 514/912 |
| 5,277,901 | 1/1994 | Vigh et al. | 514/912 |
| 5,424,078 | 6/1995 | Dziabo et al. | 514/912 |

OTHER PUBLICATIONS

CA117: 178175, Albertha et al., 1991.
Remington's Pharmaceutical Sciences, 18th Edition, p. 1587–1592, 1990.

*Primary Examiner*—Edward J. Webman
*Attorney, Agent, or Firm*—Pennie & Edmonds

[57] ABSTRACT

The invention provides novel compositions of matter containing water-insoluble steroid drugs suitable for therapeutic use. The invention provides stable aqueous suspensions of water-insoluble steroid drugs of particle sizes of ≦15 μm which remain in such a state so as to allow for immediate suspension, when desired, even after extended periods of settling.

17 Claims, No Drawings

SUSPENSION OF LOTEPREDNOL ETABONATE FOR EAR, EYE, OR NOSE TREATMENT

FIELD OF INVENTION

The invention relates to aqueous suspensions for treatment of ophthalmic and otolaryngological inflammations.

BACKGROUND OF THE INVENTION

Numerous drugs are prepared in the form of suspensions for ophthalmic, oral, otic, nasal respiratory topical, and parenteral applications. Formulation of pharmaceutical dosages of water-insoluble drugs as suspensions is frequently hampered by the subsequent formation of cakes resulting from aggregation of the suspended material. Polymeric compounds (e.g. polyvinyl pyrrolidone, polyvinyl alcohol, dextran) are commonly used to stabilize such suspensions. An alternative approach to the preparation of such drugs is to enhance the solubility of the drugs within the formulation by vehicles including emulsions, liposomes, and cyclodextrins. However, certain drugs, in their therapeutic concentrations, are not sufficiently stabilized or solubilized by these methods for the above-mentioned applications.

Topical steroids such as corticosteroids are commonly used for anti-inflammatory therapy of the eye, especially for treating inflammatory conditions of the palpebral or bulbar conjunctiva, cornea and anterior segment of the globe. Common therapeutic applications for steroids include allergic-conjunctivitis, ache rosacea, superficial punctate keratitis and iritis cyclitis. Steroids also are used to ameliorate inflammation associated with corneal injury due to chemical or thermal burns, or penetration of foreign bodies. Such conditions may result from surgery, injury, allergy or infection to the eye and can cause severe discomfort.

Despite their therapeutic advantages, topical ocular use of corticosteroids is associated with a number of complications, including posterior subcapsular cataract formation, elevation of intraocular pressure, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

Topical steroids for treating ocular inflammations can be based on soft drugs. Soft drugs, as is known in the art, are designed to provide maximal therapeutic effect and minimal side effects. By one approach, synthesis of a "soft drug" can be achieved by structurally modifying a known inactive metabolite of a known active drug to produce an active metabolite that undergoes a predictable one-step transformation in-vivo back to the parent, (see, U.S. Pat. Nos. 4,996,335 and 4,710,495 for soft steroids) inactive metabolite. "Soft drugs" therefore are biologically active chemical components characterized by predictable in vivo metabolism to non-toxic derivatives after they provide their therapeutic effect.

Pharmaceutical compositions of water-insoluble drugs such as corticosteroids in aqueous suspensions for ocular and other uses must satisfy constraints imposed by physiological compatibilities such as pH, osmolality, and particle size of the suspended steroids. Furthermore, these compositions must meet requirements for preservative efficiency and ease of suspension over extended periods of time.

Therapeutic suspensions of corticosteroids typically employ polymeric compounds such as polyvinyl pyrrolidone ("PVP") and polyvinyl alcohol ("PVA") as suspending agents in concentrations ranging from 0.1 to 10% (U.S. Pat. No. 2,861,920). Combinations of polymeric compounds such as PVP, PVA, sodium carboxymethylcellulose ("CMC"), and dextran, with surface-active agents such as Polysorbate 80, Polysorbate 20, and tyloxapol also have been used to stabilize corticosteroid suspensions intended for ophthalmic, nasal, and otic uses.

The amounts of polymeric compounds and surface active agents must be determined to provide stability to suspensions of corticosteroids. Excessive amounts of polymeric compounds may hamper the antimicrobial effects of preservatives added to the suspension. Also, pharmaceutical ocular and nasal dosages of these suspensions either must be buffered or have an appropriate pH with no buffering capacity. These suspensions also should be isotonic.

Loteprednol etabonate ("LE") is a known soft corticosteroid based on the known inactive metabolite prednisolone acetate of the active drug prednisolone. See U.S. Pat. Nos. 4,996,335 and 4,710,495.

LE is an analog of prednisolone that does not have a 20-keto group attached to the 17β-position. Instead, the 17β-position is occupied with a metabolically-labile ester function. In biological systems, LE is hydrolysed to the inactive carboxylic acid metabolite (PJ-91) that does not bind to glucocorticoid receptors. LE also provides superior safety by reducing the risk of steroid induced cataracts and elevation of intra-ocular pressure. The lability of LE to enzymes located in the blood and/or liver also reduces the likelihood of systemic side effects. LE therefore provides therapeutic advantages over other corticosteroids by providing efficacy similar to its parent compound, namely, prednisolone acetate, with fewer deleterious systemic side effects. Soft steroids have the potential advantage of treating inflammation without inducing elevation of intraocular pressure. In addition, soft steroids can provide the added benefit of a lower tendency to induce cataracts which may result from interaction of corticosteroids with the ocular lens proteins.

Formulation of stable aqueous suspensions of LE for ocular applications and other uses, however, has been hampered by agglomeration of the steroid particles. Unexpectedly, common tonicity agents such as aqueous solutions containing 0.9% NaCl, 0.1% EDTA, or phosphate buffer, even in concentrations as low as 1 mM, can not be employed to provide stable aqueous suspensions of corticosteroids such as LE.

A need therefore exists for aqueous suspensions of corticosteroids such as LE which can be formulated without agglomeration. A further need exists for aqueous suspensions which have therapeutically effective amounts of corticosteroids such as LE but which avoid the problems associated with the steroid suspensions of the prior art.

SUMMARY OF THE INVENTION

The invention provides novel compositions of matter containing water-insoluble drugs suitable for therapeutic use. The invention provides stable aqueous suspensions of water-insoluble drugs of mean particle sizes of <15 μm which remain in such a state so as to allow for immediate suspension, when desired, even after extended periods of settling.

More particularly, the invention is directed to aqueous suspensions of soft corticosteroids such as loteprednol etabonate suitable for therapeutic use in the eye, ear, or nose. The aqueous suspensions of LE are surprisingly stable and can remain in a state suitable for immediate suspension when desired, even after extended periods of settling. The suspensions of the invention, moreover, do not cause discomfort upon application.

The aqueous suspensions of the invention comprise component (A) of a therapeutic quantity of a "soft" steroid such as LE present as particles less than fifteen microns mean diameter, component (B) of a nonionic polymer in an aqueous medium, and component (C) of a nonionic surface active agent. The molar ratio of (A):(B):(C) can vary from about 1:0.01:0.05 to about 1:20:1. The steroid of component (A) preferably is loteprednol etabonate added to obtain a final concentration in the suspension of about 0.2–2.0%, preferably about 0.5–1.0% (w/w). The nonionic polymer of component (B) is present in an amount of between about 0.2 to 2% by weight, and preferably between about 0.4 to 1.5%, and more preferably between about 0.4 to 1%. The molar ratio of component (A) to component (B) typically is in the range of about 1:0.01 to about 1:20, preferably about 1:0.5 to about 1:3. The surfactant of component (C) is present in an amount of about 0.05 to 1% by weight. The compositions also may, if necessary, include component (D) of a tonicity agent for producing isotonicity, and component (E) of preservative(s) in an aqueous medium.

In a preferred aspect, stable aqueous suspensions of LE are provided by preparing aqueous suspensions of LE in concentrations of about 0.5–1.0% with about 0.6% PVP, about 2–2.8% glycerol, preferably about 2.2–2.6% glycerol, most preferably about 2.4% glycerol, and about 0.05 to 0.1% tyloxapol, preferably about 0.1 to 0.6% tyloxapol. Accepted preservatives such as benzalkonium chloride and disodium edentate ("EDTA") may be included in the suspensions of the invention in concentrations sufficient for effective antibacterial action, preferably about 0.01–0.025%, based on the weight of the suspension. However, it is essential that these components (A)–(D) be nonionic insofar as possible since it has now been discovered that the presence of ions is the major cause of caking. Thus, a preferred tonicity agent would be mannitol or glycerol rather than the commonly used sodium chloride.

Stable aqueous suspensions of the invention can be produced over a broad range of pH values. A pH of about 4.5–7.4 especially is useful for preparing the stable LE suspensions of the invention.

Having briefly summarized the invention, the invention will now be described in detail by reference to the following specification and non-limiting examples. Unless otherwise specified, all percentages are by weight and all temperatures are in degrees Celsius.

DETAILED DESCRIPTION OF THE INVENTION

Therapeutic suspensions of LE for ophthalmic or otolaryngological uses are made by aseptic preparation. Purity levels of all materials employed in the suspensions of the invention exceed 98%. The suspensions of the invention are prepared by thoroughly mixing the drug (component (A)), suspending agent (component (B)), and surface active agent (component (C)). Optionally, tonicity agents (component (D)) and preservatives (component (E)) may be included.

Drugs of component (A), preferably soft steroids, most preferably LE, can be employed. Also other steroids such as beclomethasone, betamethasone, fluocinolone, fluorometholone, exednisolone, may be employed. The suspensions of component (A) of the invention have a particle size of about 0.1–30μ, preferably about 1–20μ, most preferably about 2–10 microns in mean diameter. LE in this size range is commercially available from suppliers such as the Sipsy Co., (Avrillé, France) The nonionic polymer of component (B) can be any nonionic water-soluble polymer. Typical compounds such as PVP, PVA, HPMC or dextran can be used at a concentration of about 0.2–2%, and preferably between about 0.4 to 1.5%, and more preferably between 0.4 to 1%.

Component (C) is a surface-active agent that is acceptable for ophthalmic or otolaryngological uses. Preferably, this surfactant is non-ionic. Useful surface active agents include but are not limited to polysorbate 80, tyloxapol, TWEEN 80 (ICI America Inc., Wilmington, Del.), PLURONIC F-68 (from BASF, Ludwigshafen, Germany) and the poloxamer surfactants can also be used. These surfactants are nonionic alkaline oxide condensates of an organic compound which contains hydroxyl groups. The concentration in which the surface active agent may be used is only limited by neutralization of the bacteriocidal effects on the accompanying preservatives, or by concentrations which may cause irritation. Preferably, the concentration of component (C) is about 0.05 to 1%, and more preferably 0.1 to 0.6% by weight based on the weight of the suspension.

The tonicity agents of component (D) can be nonionic diols, preferably glycerol, in sufficient amounts to achieve isotonicity. The nonionic tonicity agents can be present in an amount of about 2 to 2.8% by weight, and preferably about 2.2 to 2.6%.

The nonionic polymeric compounds of component (B), and the surface active agents of component (C) have good solubility in water, have sufficient number of hydroxyl groups to interact with the steroid, and have mild effects on the viscosity of the suspension. Final viscosity should not exceed 80-centipoise.

The suspensions of the invention also may include additional therapeutic drugs such as drugs for treating glaucoma, anti-inflammatory drugs, antibiotic drugs, anti-cancer drugs, anti-fungal drugs and anti-viral drugs. Examples of anti-glaucoma drugs include but are not limited to timolol-base, betaxalol, athenolol, levobanolol, epinenephrin, dipivalyl, oxonolol, acetazilumide-base and methazalomide. Examples of anti-inflammatory drugs include but are not limited to non-steroids such as piroxicam, indomethacine, naproxen, phenylbutazone, ibuprofen and diclofenac. Additional therapeutic materials which may be employed include but are not limited to tobramycin, gentamycin or other antibiotics.

Health regulations in various countries generally require that ophthalmic preparations shall include a preservative. Many well known preservatives that have been used in ophthalmic preparations of the prior art, however, cannot be used in the preparations of the invention, since those preservatives may no longer be considered safe for ocular use, or may interact with the surfactant employed in the suspension to form a complex that reduces the bacteriocidic activity of the preservative.

The preservatives of component (E) employed in the suspensions of the invention therefore are chosen to not interact with the surface active agent to an extent that the preservatives are prevented from protecting the suspension from microbiological contamination. In a preferred embodiment benzalkonium chloride may be employed as a safe preservative, most preferably benzalkonium chloride with EDTA. Other possible preservatives include but are not limited to benzyl alcohol, methyl parabens, propyl parabens, thimerosal, chlorbutanol and benzethonium chlorides. Preferably, a preservative (or combination of preservatives) that will impart standard antimicrobial activity to the suspension and protect against oxidation of components (A)–(D) is employed.

Without further elaboration, it is believed that one skilled in the art can, using the preceding description, utilize the present invention to its fullest extent. The following preferred specific embodiments therefore are to be construed as merely illustrative, and not limitative of the remainder of the disclosure in any way whatsoever. In the following examples, all temperatures are set forth in degrees Celsius; unless otherwise indicated, all parts and percentages are by weight.

EXAMPLES 1–37

Each of Examples 1–37 are prepared by dissolving the suspending agent (Component B) in water by gentle mechanical mixing. Subsequently, the surfactant (Component C), the tonicity agent(s) and the preservatives (Components (D) and (E), respectively) are added in that order. The solution is then sterilized by filtration or autoclaving. LE, presterilized by irradiation, is added aseptically to the solution, and the disperson is then mixed at 12,000 rpm for one minute. The amounts of these components are shown in Table 1.

| Example Number | LE | TWEEN 80 | Tyloxapol | POLOXAMER-188 | HPMC[1] | PVA | PVP | Dextran | Osmolarity Agent | EDTA[4] | BKA[5] |
|---|---|---|---|---|---|---|---|---|---|---|---|
| 1 | 0.5 | — | 0.2 | — | — | 0.6 | — | — | — | — | — |
| 2 | 0.5 | 0.2 | — | — | — | — | 0.2 | — | 10 mM PBS[2] | — | — |
| 3 | 0.5 | — | 0.4 | — | 0.2 | — | 0.4 | — | — | — | — |
| 4 | 0.5 | — | 0.2 | — | — | 0.2 | — | — | 10 mM PBS | — | — |
| 5 | 0.5 | 0.6 | — | — | 0.4 | — | — | — | 100 mM PBS | — | — |
| 6 | 0.5 | 0.4 | — | — | — | 1.4 | — | — | 5 mM PBS | — | 0.001 |
| 7 | 1 | — | 0.2 | — | — | — | 1 | — | — | — | — |
| 8 | 1 | — | 0.6 | — | — | — | 1.4 | — | — | — | — |
| 9 | 1 | 0.6 | — | — | — | — | 1.4 | — | — | — | — |
| 10 | 0.5 | — | 0.4 | — | — | 1 | — | — | 0.9% saline[3] | — | 0.001 |
| 11 | 0.5 | 0.4 | — | — | — | 1 | — | — | 0.9% saline | — | 0.001 |
| 12 | 0.5 | 0.6 | — | — | — | — | 2 | — | 2.4% glycerol | 0.01 | 0.01 |
| 13 | 0.5 | — | 0.3 | — | — | — | 1.5 | — | 2.4% glycerol | 0.01 | 0.01 |
| 14 | 0.5 | — | 0.3 | — | — | — | 0.6 | 0.5 | 2.4% glycerol | 0.01 | 0.015 |
| 15 | 0.5 | 0.4 | — | — | — | 1.4 | — | — | 2.4% glycerol | — | 0.001 |
| 16 | 1 | — | 0.2 | — | — | — | 1 | — | 2.4% glycerol | — | 0.01 |
| 17 | 0.5 | — | 0.6 | — | — | 1.4 | — | — | 2.4% glycerol | — | 0.01 |
| 18 | 0.5 | — | — | 0.6 | — | — | 2 | — | 2.4% glycerol | 0.01 | 0.004 |
| 19 | 0.5 | 0.4 | — | — | — | — | — | 1.6 | 2.4% glycerol | 0.01 | 0.004 |
| 20 | 0.5 | — | 0.4 | — | — | — | — | 2.4 | 2.4% glycerol | 0.01 | 0.01 |
| 21 | 0.5 | — | 0.3 | — | — | — | 1 | — | 2.4% glycerol | 0.01 | 0.01 |
| 22 | 0.5 | 0.6 | — | — | — | 1.4 | — | — | 2.4% glycerol | — | — |
| 23 | 0.5 | 0.6 | — | — | — | 1.4 | — | — | 2.4% glycerol | — | 0.004 |
| 24 | 0.5 | 0.6 | — | — | — | — | — | 2 | 2.4% glycerol | 0.01 | 0.01 |
| 25 | 0.5 | — | 0.3 | — | — | — | 0.6 | — | 2.4% glycerol | 0.01 | 0.01 |
| 26 | 0.5 | — | 0.3 | — | — | — | 0.6 | 0.5 | 2.4% glycerol | 0.01 | 0.01 |
| 27 | 1 | — | 0.3 | — | — | — | 0.6 | 0.5 | 2.4% glycerol | 0.01 | 0.015 |
| 28 | 1 | — | 0.3 | — | — | — | 0.6 | — | 2.4% glycerol | 0.01 | 0.015 |
| 29 | 1 | — | 0.1 | — | — | — | 0.4 | — | 2.4% glycerol | 0.01 | 0.01 |
| 30 | 0.5 | — | 0.2 | — | — | — | 0.6 | — | 2.4% glycerol | 0.01 | 0.01 |
| 31 | 1 | — | 0.2 | — | — | — | 0.6 | — | 2.4% glycerol | 0.01 | 0.01 |
| 32 | 1 | — | 0.2 | — | — | — | 0.8 | — | 2.4% glycerol | 0.01 | 0.015 |
| 33 | 0.5 | — | 0.3 | — | — | — | 1.5 | — | 2.4% glycerol | 0.01 | 0.015 |
| 34 | 1 | — | 0.4 | — | — | — | 0.4 | — | 2.4% glycerol | 0.01 | 0.01 |
| 35 | 0.5 | — | 0.3 | — | — | — | 0.6 | 0.3 | 2.4% glycerol | 0.01 | 0.01 |
| 36 | 0.5 | — | 0.1 | — | — | — | 0.4 | 0.3 | 2.4% glycerol | 0.01 | 0.01 |
| 37 | 0.5 | — | 0.3 | — | — | — | 0.6 | — | 2.4% glycerol | 0.01 | 0.015 |

SAMPLE COMPOSITION (% w/w)

[1]hydroxypropylmethyl cellulose
[2]phosphate buffered physiological saline
[3]sodium chloride
[4]ethylene diamine tetraacetic acid
[5]benzalkonium chloride

SIZE DETERMINATION

The size distributions of the LE particles in the samples of Table 1 are measured with a Coulter® LS 130 instrument. An acceptable average particle size for ophthalmic suspensions is ≦15 μm. The results appear in Table 2.

TABLE 2

| Example Number | Particle Size(s) (μm) and Fraction of Total Population | | | |
|---|---|---|---|---|
| | Population A | A % | Population B | B % |
| 1 | 3.906 +/– 2.677 | 86.62 | 53.67 +/– 13.13 | 13.38 |
| 2 | 112.7 +/– 13.27 | 100 | — | — |
| 3 | 3.526 +/– 1.706 | 100 | — | — |
| 4 | 111.4 +/– 18.59 | 100 | — | — |

| | | | | |
|---|---|---|---|---|
| 5 | 23.52 +/− 20.58 | 100 | — | — |
| 6 | 32.83 +/− 2.563 | 48.74 | 94.06 +/− 40.57 | 51.26 |
| 7 | 4.596 +/− 2.698 | 92.43 | 57.91 +/− 18.14 | 7.57 |
| 8 | 3.805 +/− 2.417 | 93.14 | 62.38 +/− 20.38 | 6.86 |
| 9 | 6.591 +/− 3.566 | 100 | — | — |
| 10 | 3.828 +/− 2.693 | 17.52 | 96.28 +/− 38.13 | 82.48 |
| 11 | 3.888 +/− 2.69 | 10.95 | 110.1 +/− 58.02 | 85.98 |
| 12 | 3.559 +/− 1.469 | 5.62 | 82.84 +/− 13.08 | 94.38 |
| 13 | 2.932 +/− 2.32 | 3.52 | 100.1 +/− 24,56 | 96.48 |
| 14 | 88.52 +/− 30.19 | 100 | — | — |
| 15 | 3.652 +/− 2.692 | 100 | — | — |
| 16 | 3.851 +/− 2.401 | 100 | — | — |
| 17 | 3.969 +/− 2.572 | 100 | — | — |
| 18 | 4.926 +/− 2.955 | 92.29 | 41.59 +/− 7.125 | 7.71 |
| 19 | 4.429 +/− 2,732 | 100 | — | — |
| 20 | 3.980 +/− 2.566 | 100 | — | — |
| 21 | 3.633 +/− 2.457 | 100 | — | — |
| 22 | 4.716 +/− 2.762 | 100 | — | — |
| 23 | 4.789 +/− 2.823 | 100 | — | — |
| 24 | 4.528 +/− 2.552 | 100 | — | — |
| 25 | 5.261 +/− 2.990 | 100 | — | — |
| 26 | 5.262 +/− 3.013 | 100 | — | — |
| 27 | 5.204 +/− 2.985 | 100 | — | — |
| 28 | 4.918 +/− 2.832 | 100 | — | — |
| 29 | 4.126 +/− 2.390 | 100 | — | — |
| 30 | 12.45 +/− 10.91 | 100 | — | — |
| 31 | 3.976 +/− 2.245 | 100 | — | — |
| 32 | 3.789 +/− 1.609 | 100 | — | — |
| 33 | 3.821 +/− 2.181 | 46.77 | 107.3 +/− 14.74 | 53.23 |
| 34 | 3.813 +/− 2.305 | 100 | — | — |
| 35 | 3.385 +/− 1.506 | 78.44 | 25.16 +/− 1.421 | 21.56 |
| 36 | 3.737 +/− 2.044 | 100 | — | — |
| 37 | 3.965 +/− 2.229 | 100 | — | — |

1. In the Coulter particle size analysis two distinct populations of particles were sometimes discerned. In these cases the two populations are denoted as populations A and B. If only a single population was detected it is denoted population A.

EVALUATION OF SUSPENDIBILITY OVER TIME

Samples containing particles with desirable size distributions (average of 2–10 μm) are tested for stability using accelerated stability tests as well as "real time" studies.

Accelerated stability studies are performed by subjecting the samples to a centrifugal force of 5000×G for two minutes. The suspendibility of the settled material is tested by measuring the number of seconds of wrist shaking required to eliminate visible residue attached to the container. Since existing marketed products require as much as sixty seconds of wrist shaking to suspend the entire amount of settled residue, ten seconds is determined to be an acceptable amount of time to suspend the residue. The results are shown in Table 3.

TABLE 3

RESUSPENSION OF LE SUSPENSIONS WHICH HAVE UNDERGONE ACCELERATED AND NATURAL[1] SETTLING

| | Accelerated | Suspension of naturally settled material[1] | |
|---|---|---|---|
| Example Number | Stability (time to resuspend)[2] | Initial Value (# inversions) | Months Tested[3] |
| 15 | 15 | — | 10(I) |
| 16 | 5 | — | 10(I) |
| 17 | 5 | — | 10(I) |
| 18 | 5 | — | 9 |
| 19 | 5 | — | 9 |
| 20 | — | 67 | 9 |
| 21 | — | 46 | 9 |
| 22 | — | 83 | 9 |
| 23 | — | 37 | 9 |
| 24 | — | — | 6(I) |

TABLE 3-continued

RESUSPENSION OF LE SUSPENSIONS WHICH HAVE UNDERGONE ACCELERATED AND NATURAL[1] SETTLING

| | Accelerated | Suspension of naturally settled material[1] | |
|---|---|---|---|
| Example Number | Stability (time to resuspend)[2] | Initial Value (# inversions) | Months Tested[3] |
| 25 | 5 | 27 | 8 |
| 26 | 5 | 22 | 6(I) |
| 27 | 5 | 35 | 6(I) |
| 28 | 5 | 35 | 8(I) |
| 29 | — | 49 | 7 |
| 30 | 5 | 25 | 7 |
| 31 | 5 | 43 | 7 |
| 32 | — | 74 | 7 |
| 33 | — | 136 | 3(I) |
| 34 | — | 40 | 7 |
| 35 | — | 18 | 7 |
| 36 | — | 48 | 7 |
| 37 | — | 46 | 8 |

[1] Refers to settling, at room temperature, on an open shelf
[2] Number of seconds of wrist shaking to suspend material that was settled by application of 5000 × G for 2 minutes.
[3] During the test period, samples were periodically examined to verify the retention of the initial values "I" indicates instability for the noted period, i.e., agglomeration.

The results shown in Table 3 show samples which do not form agglomerates during the longest period of observation. Acceptable samples require ≦100 gentle inversions following the indicated period of settling.

The stability of suspensions intended for multiple doses is supported by the addition of preservatives which prevent potential microbiological growth. The indicated preparations are prepared under aseptic conditions and aliquots of each material are exposed to the indicated microbiological organisms for four weeks and evaluated for growth as described in the U.S. Pharmacopeia. The results, shown in Table 4, indicate whether the preservative was effective (+) or ineffective (−) according to U.S.P. requirements.

TABLE 4

| | Challenge Microorganism | | | | |
|---|---|---|---|---|---|
| Example | Staph. aureus | P. aerug. | Candida albicans | Asper. niger | E. coli |
| 23 | + | − | − | − | ND |
| 24 | + | − | − | − | ND |
| 25 | + | − | − | + | ND |
| 26 | + | + | + | + | ND |
| 27 | + | + | − | + | + |
| 28 | + | + | + | + | + |
| 29 | + | + | + | + | ND |
| 30 | + | + | + | + | + |
| 31 | + | + | + | + | + |
| 32 | + | + | + | + | + |

ND: denotes not done; (+) denotes challenge withstood; (−) denotes unacceptable microbe growth
The test was performed according to U.S.P. specifications.

UNIDOSE SUSPENSIONS WITHOUT PRESERVATIVES

Compositions with satisfactory particle sizes and stabilities for unidose suspensions without preservatives appear in Table 5. These compositions are satisfactory for ophthalmic or otolaryngological uses when prepared under aseptic conditions and packaged in containers for single doses.

TABLE 5

COMPOSITIONS OF EXEMPLARY LE FORMULATIONS FOR UNIDOSE APPLICATION

| Ex. No. | LE | Tween 80 | Tyloxapol | Poloxamer-188 | PVA | PVP | dextran | glycerol | Purified Water |
|---|---|---|---|---|---|---|---|---|---|
| 1 | 1 | 0.6 | — | — | — | 1.4 | — | 2.4 | Remainder |
| 2 | 0.5 | — | — | 0.6 | — | 2 | — | 2.4 | Remainder |
| 3 | 0.5 | 0.4 | — | — | — | — | 1.6 | 2.4 | Remainder |
| 4 | 0.5 | — | 0.4 | — | — | — | 2.4 | 2.4 | Remainder |
| 5 | 0.5 | — | 0.3 | — | — | 1 | — | 2.4 | Remainder |
| 6 | 0.5 | — | 0.6 | — | 0.8 | — | — | 2.4 | Remainder |
| 7 | 0.5 | 0.6 | — | — | 1.4 | 0.8 | — | 2.4 | Remainder |
| 8 | 0.5 | 0.6 | — | — | — | — | 2 | 2.4 | Remainder |
| 9 | 0.5 | 0.6 | — | — | — | — | 2.4 | 2.4 | Remainder |
| 10 | 0.5 | — | 0.3 | — | — | 0.6 | — | 2.4 | Remainder |
| 11 | 0.5 | — | 0.3 | — | — | 0.6 | 0.5 | 2.4 | Remainder |
| 12 | 1 | — | 0.3 | — | — | 0.6 | 0.5 | 2.4 | Remainder |
| 13 | 1 | — | 0.3 | — | — | 0.6 | — | 2.4 | Remainder |
| 14 | 1 | — | 0.1 | — | — | 0.4 | — | 2.4 | Remainder |
| 15 | 0.5 | — | 0.2 | — | — | 0.6 | — | 2.4 | Remainder |
| 16 | 1 | — | 0.2 | — | — | 0.6 | — | 2.4 | Remainder |
| 17 | 1 | — | 0.4 | — | — | 0.6 | — | 2.4 | Remainder |
| 18 | 1 | — | 0.2 | — | — | 0.8 | — | 2.4 | Remainder |
| 19 | 1 | — | 0.4 | — | — | 0.4 | — | 2.4 | Remainder |
| 20 | 0.5 | — | 0.4 | — | — | 0.4 | — | 2.4 | Remainder |
| 21 | 0.5 | — | 0.3 | — | — | 0.6 | 0.3 | 2.4 | Remainder |
| 22 | 0.5 | — | 0.1 | — | — | 0.4 | 0.3 | 2.4 | Remainder |

We claim:

1. A composition for ophthalmic or otolaryngological anti-inflammatory use comprising:

(A) a corticosteroid having a particle size of 0.1 to 30 microns in diameter in an amount of about 0.2 to 2% by weight;

(B) a nonionic polymer in an aqueous medium;

(C) a nonionic surface active agent in an amount sufficient to retain the corticosteroid in suspension; and (D) a nonionic tonicity agent in an amount sufficient to achieve isotonicity, wherein the molar ratio of (A):(B):(C) is between about 1:20:1 and about 1:0.01:0.5.

2. The composition of claim 1 wherein the corticosteroid is selected from the group consisting of soft steroids having anti-inflammatory activity.

3. The composition of claim 1 wherein the corticosteroid is loteprednol etabonate and is present in an amount of about 0.5 to 1% by weight.

4. The composition of claim 3 wherein said corticosteroid has a particle size less than about fifteen microns.

5. The composition of claim 1 further including a preservative for preventing microbial formation in said composition and in an amount of about 0.01 to 0.025% by weight.

6. The composition of claim 5 wherein said preservative is benzalkonium chloride.

7. The composition of claim 6 further comprising disodium edetate.

8. The composition of claim 1 wherein said nonionic polymer is selected from the group consisting of polyvinylpyrrolidone, polyvinyl alcohol, or dextran and is present in an amount of about 0.2 to 2% by weight and wherein the nonionic surfactant is present in an amount of about 0.05 to 1% by weight.

9. The composition of claim 1 wherein said nonionic polymer is polyvinylpyrrolidone and is present in an amount of about 0.4 to 1% by weight.

10. The composition of claim 1 wherein said nonionic surface active agent is tyloxapol and is present in an amount of about 0.1 to 0.6% by weight.

11. The composition of claim 1 further comprising an additional therapeutic drug in admixture with said corticosteroid, wherein said additional therapeutic drug is selected from the group consisting of betaxalol, athenolol, livobanolol, epinenephrin, dipivalyl, oxonolol, acetazilumide-base, methazalomide, tobramycin, gentamycin, piroxicam, indomethacin, naproxen, phenylbutazone, ibuprofen, and diclofenac-acid.

12. A composition for ophthalmic or otolaryngological anti-inflammatory use according to claim 1 in which the nonionic tonicity agent is glycerol in an amount 2 to 2.8%.

13. A composition for ophthalmic or otolaryngological anti-inflammatory use comprising a nonionic polymer in an aqueous medium, a nonionic tonicity agent in an amount effective to product isotonicity, and a nonionic surface active agent in an amount sufficient to retain the polymer and tonicity agent in the aqueous medium, and further comprising a corticosteroid having a particle size of 0.1 to 30 microns in diameter in an amount of about 0.2 to 2% by weight, wherein the molar ratio of corticosteroid to nonionic polymer to nonionic surface active agent is between about 1:20:1 and about 1:0.01:0.05.

14. The composition of claim 13 wherein said nonionic tonicity agent is a nonionic diol and is present in an amount of about 2 to 2.8% by weight.

15. The composition of claim 13 wherein the nonionic polymer is present in an amount of about 0.2 to 2% by weight; the nonionic tonicity agent is present in an amount of about 2 to 2.8% by weight; and the nonionic surface active agent is present in an amount of about 0.05 to 1% by weight.

16. The composition of claim 13 further comprising a preservative of benzalkonium chloride, disodium edetate, and mixtures thereof in an amount of about 0.01 to 0.025% by weight.

17. The composition of claim 13 wherein the nonionic polymer is polyvinyl pyrrolidone and is present in an amount of about 0.4 to 1% by weight, the nonionic tonicity agent is mannitol or a diol and is present in an amount of about 2 to 2.8% by weight, and the nonionic surface active agent is tyloxapol and is present in an amount of about 0.1 to 0.6% by weight.

* * * * *

UNITED STATES PATENT AND TRADEMARK OFFICE
CERTIFICATE OF CORRECTION

PATENT NO. : 5,540,930

DATED : July 30, 1996

INVENTOR(S) : Guy et al.

It is certified that error appears in the above-identified patent and that said Letters Patent is hereby corrected as shown below:

Claim 1, line 39: "0.5" should read --0.05--.

Signed and Sealed this

Twenty-second Day of July, 1997

Attest:

BRUCE LEHMAN

Attesting Officer

Commissioner of Patents and Trademarks